(12) United States Patent
Miyoshi

(10) Patent No.: US 8,691,589 B2
(45) Date of Patent: Apr. 8, 2014

(54) METHOD FOR DETECTING FORMATION OF G-QUADRUPLEX

(71) Applicant: Panasonic Corporation, Osaka (JP)

(72) Inventor: Daisuke Miyoshi, Kyoto (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 13/900,227

(22) Filed: May 22, 2013

(65) Prior Publication Data

US 2013/0288380 A1 Oct. 31, 2013

Related U.S. Application Data

(63) Continuation of application No. PCT/JP2012/003921, filed on Jun. 15, 2012.

(30) Foreign Application Priority Data

Aug. 11, 2011 (JP) .................. 2011-175808

(51) Int. Cl.
*G01N 21/64* (2006.01)
*C12Q 1/68* (2006.01)

(52) U.S. Cl.
USPC .............. 436/94; 436/79; 436/164; 436/172; 435/6.1; 435/6.19; 536/23.1

(58) Field of Classification Search
USPC .......... 436/73, 79, 92, 94, 96, 106, 119, 164, 436/166, 172; 435/6.1, 6.19; 536/23.1
See application file for complete search history.

(56) References Cited

U.S. PATENT DOCUMENTS

| | | | |
|---|---|---|---|
| 8,119,347 B2* | 2/2012 | Yaku et al. | 435/6.1 |
| 8,232,054 B2* | 7/2012 | Yaku et al. | 435/6.1 |
| 2010/0173306 A1 | 7/2010 | Yaku et al. | |

FOREIGN PATENT DOCUMENTS

JP 2010-030999 A 2/2010

OTHER PUBLICATIONS

Gabelica et al. Biochemistry, vol. 52, 2013, pp. 5620-5628.*
Mohanty et al. Journal of the American Chemical Society, vol. 135, 2013, pp. 367-376.*
Tong et al. Biosensors and Bioelectronics, vol. 49, 2013, pp. 420-425.*
International Search Report issued in International Patent Application No. PCT/JP2012/003921 mailed on Sep. 18, 2012.
Lubitz, Irit et al. "Specific High-Affinity Binding of Thiazole Orange to Triplex and G-Quadruplex DNA" Biochemistry. vol. 49 / No. 17, pp. 3567-3574. 2010.
Kovalska, Vladyslava et al. "Mono and Trimethine Cyanines Cyan 40 and Cyan 2 as Probes for Highly Selective Fluorescent Detection of Non-canonical DNA Structures." Springer, vol. 21 / No. 1, pp. 223-230, Published online Sep. 1, 2010.
Chang, Cheng-Chung et al. "Detection of Quadruplex DNA Structures in Human Telomeres by a Fluorescent Carbazole Derivative" Analytical Chemistry, vol. 76 / No. 15, pp. 4490-4494, Aug. 1, 2004.

(Continued)

*Primary Examiner* — Maureen Wallenhorst
(74) *Attorney, Agent, or Firm* — McDermott Will & Emery LLP

(57) ABSTRACT

The method of the present disclosure determines whether a target DNA forms a G-quadruplex using a phenomenon in which thioflavin T generates a strong fluorescence when reacted with the G-quadruplex in the presence of potassium ions.

4 Claims, 12 Drawing Sheets

(56) References Cited

OTHER PUBLICATIONS

Chang, Ta-Chau et al. "Detection of G-Quadruplexes in Cells and Investigation of G-Quadruplex Structure of $d(T_2AG_3)_4$ in K+ Solution by a Carbazole Derivative: BMVC" Methods in Molecular Biology. vol. 608, pp. 183-206, 2010.

Canete, M. et al "A study of Interaction of Thioflavine T with DNA: Evidence for Intercalation" Cellular and Molecular Biology, vol. 33 / No. 2, pp. 191-199, 1987.

Allain, Clemence et al. "FRET Templated by G-Quadruplex DNA: A Specific Ternary Interaction Using an Original Pair of Donor/Acceptor Partners" J. Am. Chem. Soc. 128(36) pp. 11890-11893, 2006.

Luu, Kim Ngoc et al. "Structure of Human Telomere in K+ Solution: An Intramolecular (3+1) G-Quadruplex Scaffold" American Chemical Society, 128(30), pp. 9963-9970, 2006.

Phan, Anh Tuan et al. "Different loop arrangements of intramolecular human telomeric (3+1) G-quadruplexes in K+ solution" Nucleic Acids Research, vol. 34 / No. 19, pp. 5715-5719, 2006.

\* cited by examiner (A)

(B)

(A)

(B)

(A)

(B)

(A)

(B)

SEQUENCE LISTING

```
<160> NUMBER OF SEQ ID NOS: 10

<210> SEQ ID NO 1
<211> LENGTH: 6
<212> TYPE: DNA
<213> ORGANISM: Homo sapiens
<220> FEATURE:
<223> OTHER INFORMATION: Telomere sequence

<400> SEQUENCE: 1 ttaggg                                                              6
```

```
<210> SEQ ID NO 2
<211> LENGTH: 6
<212> TYPE: DNA
<213> ORGANISM: Homo sapiens
<220> FEATURE:
<223> OTHER INFORMATION: Telomere sequence

<400> SEQUENCE: 2 ccctaa                                                                     6

<210> SEQ ID NO 3
<211> LENGTH: 21
<212> TYPE: DNA
<213> ORGANISM: Homo sapiens
<220> FEATURE:
<223> OTHER INFORMATION: Telomere sequence

<400> SEQUENCE: 3
gggttagggt tagggttagg g                                                   21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA oligonucleotide for forming Duplex1

<400> SEQUENCE: 4
agttcaaggc gccttgaact                                                     20

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide for forming T21

<400> SEQUENCE: 5
tttttttttt tttttttttt t                                                   21

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA oligonucleotide for forming G-DNA2

<400> SEQUENCE: 6
ggggttttgg ggttttgggg ttttgggg                                            28

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence: Synthetic
      DNA oligonucleotide for forming G-DNA3

<400> SEQUENCE: 7
gggtgggtgg gtggg                                                          15

<210> SEQ ID NO 8
<211> LENGTH: 28
<212> TYPE: DNA
```

```
<213> ORGANISM: Artificial Sequence
<220> FEATURE:
<223> OTHER INFORMATION: Description of Artificial Sequence: Synthetic
      oligonucleotide DNA for forming Duplex-C

<400> SEQUENCE: 8
ccccaaaacc ccaaaacccc aaaacccc                                              28

<210> SEQ ID NO 9
<211> LENGTH: 12
<212> TYPE: DNA
<213> ORGANISM: Artificial Sequence
<220> FEATURE:
<223> OTHER INFORMATION: Description of Artificial Sequence: Synthetic
      DNA oligonucleotide for forming Duplex-AGA

<400> SEQUENCE: 9
agaagagaaa ga                                                               12

<210> SEQ ID NO 10
<211> LENGTH: 12
<212> TYPE: DNA
<213> ORGANISM: Artificial Sequence
<220> FEATURE:
<223> OTHER INFORMATION: Description of Artificial Sequence: Synthetic
      DNA oligonucleotide for forming Duplex-TCT

<400> SEQUENCE: 10
tctttctctt ct                                                               12
```

METHOD FOR DETECTING FORMATION OF G-QUADRUPLEX

RELATED APPLICATIONS

This application is the Continuation of International Application No. PCT/JP2012/003921, filed on Jun. 15, 2012, which in turn claims the benefit of Japanese Application No. 2011-175808, filed on Aug. 11, 2011, the disclosures of which Applications are incorporated by reference herein.

SEQUENCE LISTING

This application contains a Sequence Listing which has been submitted in ASCII format via EFS-Web and is hereby incorporated by reference in its entirety. Said ASCII copy, created on Jul. 19, 2013, is named 43746648_1.txt and is 2,662 bytes in size.

TECHNICAL FIELD

The present invention relates to a method for detecting a higher-order structure of DNA.

BACKGROUND ART

A human telomeric DNA includes a sequence in which a double-stranded DNA composed of 5'-TTAGGG-3' (SEQ ID NO: 1) and 5'-CCCTAA-3' (SEQ ID NO: 2, complementary strand of SEQ ID NO: 1) is repeated and a single-stranded DNA at its terminal end in which only 5'-TTAGGG-3' (SEQ ID NO: 1) is repeated. The sequence in which 5'-TTAGGG-3' (SEQ ID NO: 1) is repeated can form a quadruplex DNA structure called a G-quadruplex. The G-quadruplex is a structure constituted such that 4 guanines form a structure called a G-quartet, which in turn, stacks on one another through a π-π stacking interaction (FIG. 1). The G-quadruplex has been extensively investigated in recent years because it is considered to be associated with canceration and life of cells.

Genome-wide analyses that were recently performed with computers showed that a large number of sequences considered to be capable of forming a G-quadruplex existed in genome DNA in addition to telomeric DNA. Many of them exist in promoter regions of oncogenes including c-kit, c-myc, H-ras and K-ras genes. Therefore, these sequences considered to be capable of forming a G-quadruplex are also investigated. The fact described above suggests the possibility that the G-quadruplex plays an important role in the activity of cells.

Under the background described above, there is a need to provide a technique for conveniently analyzing whether or not a DNA considered to be capable of forming a G-quadruplex can really form a G-quadruplex. Particularly, the potassium ion concentration in the cell is about 100 to 150 mM, and therefore a technique capable of analyzing formation of a G-quadruplex under this potassium ion concentration condition is necessary. On that account, a compound that generates an especially strong fluorescence when reacting with a G-quadruplex as compared to a single-stranded DNA or a double-stranded DNA (hereinafter, referred to as a G-quadruplex probe) has been explored. In other words, the G-quadruplex probe must have a nature of generating little fluorescence when reacting with a single-stranded DNA or a double-stranded DNA, but generating a strong fluorescence when reacting with a G-quadruplex.

One of G-quadruplex probes that have been most extensively investigated in recent years is a benzothiazole derivative. The reason why the benzothiazole derivative is extensively investigated is that the benzothiazole derivative has a high water solubility and a very large variation in fluorescence intensity. For example, NPL 1 reports a G-quadruplex detection technique using Cyan 40 (chemical formula 1) and Cyan 2 (chemical formula 2). This report shows that when Cyan 2 is reacted with a G-quadruplex under such conditions that potassium ions are not present, a significantly strong fluorescence is generated as compared to a case where Cyan 2 is reacted with a double-stranded DNA. However, it is also shown that in the presence of 100 mM potassium ions, little fluorescence is detected even when Cyan 2 is reacted with a G-quadruplex. Therefore, Cyan 2 cannot be used for detection of a G-quadruplex in the presence of potassium ions. NPL 2 reports a G-quadruplex detection technique using thiazole orange (chemical formula 3) (hereinafter, referred to as TO). It is shown in this report that TO generates a strong fluorescence when it is reacted with a G-quadruplex in the presence of 100 mM potassium ions. However, it is also shown that when TO is reacted with a double-stranded DNA under the same conditions, TO generates a stronger fluorescence as compared to a case where it is reacted with a G-quadruplex. Therefore, the G-quadruplex cannot be specifically detected using TO in the presence of 100 mM potassium ions.

[Chemical formula 1]

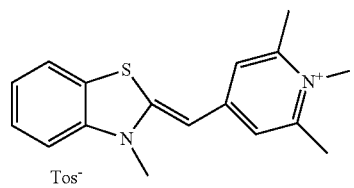

[Chemical formula 2]

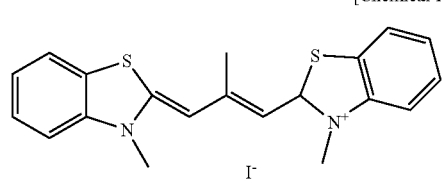

[Chemical formula 3]

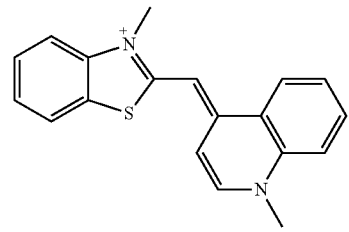

As described above, in recent years, a technique has been under development in which a G-quadruplex is specifically detected using a benzothiazole derivative as a G-quadruplex probe. However, a technique capable of specifically detecting a G-quadruplex under such conditions that potassium ions are present as in intracellular conditions has not been known.

CITATION LIST

Nonpatent Literature

NPL 1: J. Flucresc., 2011, 21 (1), 223-230
NPL 2: J. Am. Chem. Soc., 2006, 128 (36), 11890-11893.
NPL 3: J. Am. Chem. Soc., 2006, 128 (30), 9963-9970.
NPL 4: Nucleic Acids Res., 2006, 34 (19), 5715-5719.

SUMMARY OF INVENTION

Problems to be Solved by the Present Invention

A technique for conveniently analyzing whether or not a DNA considered to be capable of forming a G-quadruplex can really form a G-quadruplex in the presence of potassium ions is very useful. On that account, a G-quadruplex detection technique using a benzothiazole derivative has been extensively investigated, but a technique capable of specifically detecting a G-quadruplex in the presence of potassium ions has not been developed. Thus, the present inventors elaborately conducted investigation, and consequently discovered that in the presence of potassium ions, thioflavin T (chemical formula 4) generates a strong fluorescence when reacted with a G-quadruplex. The fluorescence intensity is significantly high as compared to a case where thioflavin T is reacted with a double-stranded DNA or a single-stranded DNA. Therefore, it has been found that according to the present invention, the G-quadruplex can be specifically detected even in the presence of potassium ions.

[Chemical formula 4]

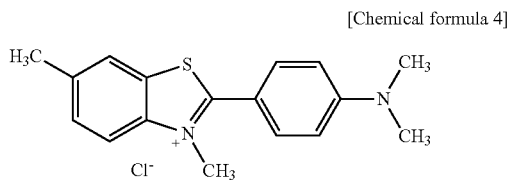

Means for Solving the Problems

The present invention for solving the above-described problem provides a method for determining whether a target DNA forms a G-quadruplex in the presence of potassium ions, wherein the method comprises the following steps of:

retaining a first sample solution containing potassium ions, thioflavin T and the target DNA under G-quadruplex forming reaction conditions; measuring a first fluorescence intensity value A at a wavelength of lambda 1, wherein the first fluorescence intensity value A is derived from thioflavin T contained in the first sample solution, and lambda 1 is 465 nanometers to 505 nanometers (both inclusive); retaining a second sample solution containing thioflavin T and the target DNA under conditions for the structure of the G-quadruplex to be destabilized; measuring a second fluorescence intensity value B at the wavelength of lambda 1, wherein the second fluorescence intensity value B is derived from thioflavin T contained in the second sample solution; and determining that the target DNA forms the G-quadruplex in the presence of potassium ions if the following inequality is satisfied:

the first fluorescence intensity value $A$–the second fluorescence intensity value $B$>0.

In the method of the present invention, it is preferable to determine that the target DNA does not form the G-quadruplex in the presence of potassium ions if the inequality of the first fluorescence intensity value A–the second fluorescence intensity value B≤0 is satisfied.

In the method of the present invention, conditions for the structure of the G-quadruplex to be destabilized are preferably such conditions that lithium is present.

In the method of the present invention, the lambda 1 is preferably 485 nanometers.

The aforementioned objects, other objects, features, and advantages of the present invention are clarified by the following detailed description of preferred embodiments with reference to accompanying drawings.

Advantageous Effects of Invention

According to the present invention, a method for specifically and quantitatively detecting a G-quadruplex in the presence of potassium ions and a method for specifically and quantitatively detecting a DNA capable of forming a G-quadruplex are provided.

DESCRIPTION OF EMBODIMENTS

Hereinafter, embodiments of the present invention are illustrated with reference to accompanying drawings.

Figure 1:
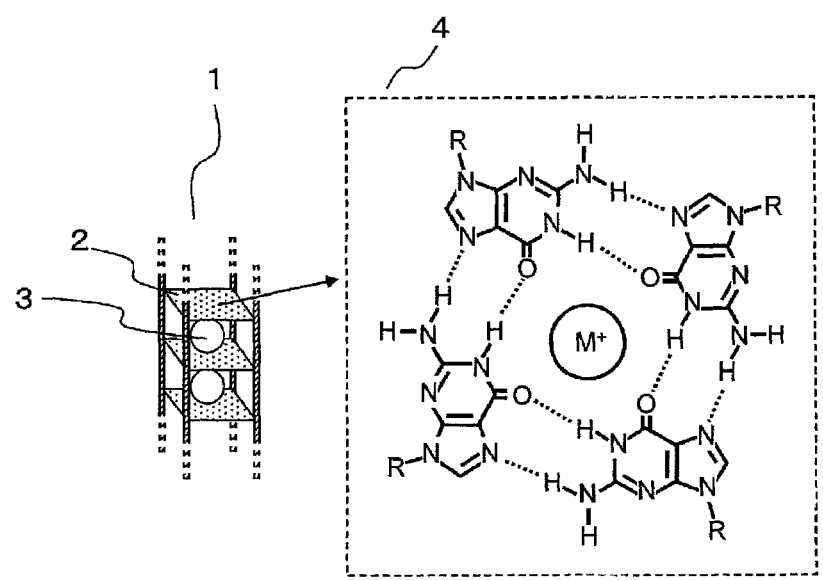
FIG. 1 shows a view for illustrating the structure of a G-quadruplex.
Figure 2:
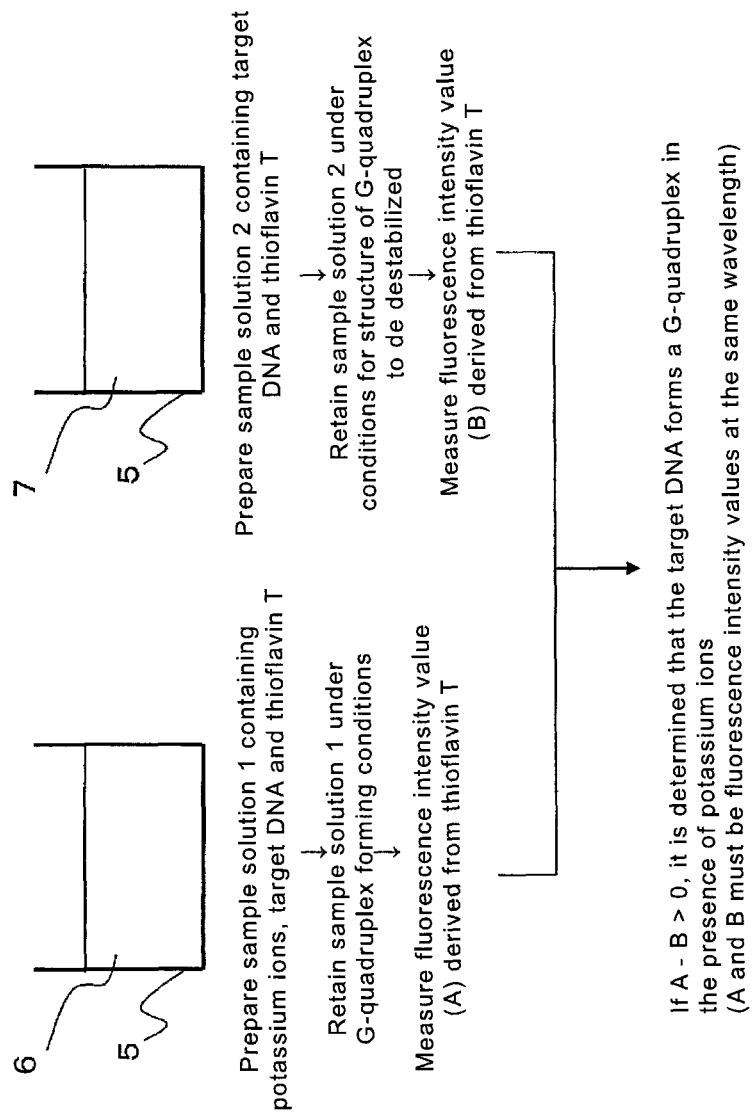
FIG. 2 shows a view for illustrating a method for investigating whether or not a target DNA forms a G-quadruplex in the presence of potassium ions in this embodiment.

In this embodiment, a method for investigating whether or not a target DNA forms a G-quadruplex in the presence of potassium ions is illustrated with reference to FIG. 2.

In this embodiment, the following steps are carried out.

(Step 1) A sample solution 1 containing potassium ions, a target DNA and thioflavin T is prepared. The order in which potassium ions, the target DNA and thioflavin T are mixed does not matter.

(Step 2) After step 1, the sample solution 1 is retained under G-quadruplex forming conditions.

(Step 3) After step 2, a fluorescence intensity value (A) derived from thioflavin T in the sample solution 1 is measured.

(Step 4) A sample solution 2 containing the target DNA and thioflavin T is retained under conditions destabilizing the structure of the G-quadruplex.

(Step 5) After step 4, a fluorescence intensity value (B) derived from thioflavin T in the sample solution 2 is measured. The fluorescence intensity values A and B are fluorescence intensity values at the same wavelength.

(Step 6) If A−B>0, it is determined that the target DNA forms a G-quadruplex in the presence of potassium ions.

In the procedure described above, thioflavin T is added in the sample solution 1 in step 1. However, it is not necessarily required that thioflavin T be added in the sample solution 1 in step 1. Thioflavin T may be added in the sample solution 1 by step 3. In the procedure described above, thioflavin T is added in the sample solution 2 in step 4. However, it is not necessarily required that thioflavin T be added in the sample solution 2 in step 4. Thioflavin T may be added in the sample solution 2 by step 5.

The present inventor has discovered that a strong fluorescence having a maximum fluorescence wavelength around 485 nm is observed when thioflavin T is reacted with a G-quadruplex. On the other hand, it has also been discovered that a fluorescence is not observed at all or only very little fluorescence is observed, if any, when thioflavin T is reacted with a single-stranded DNA or a double-stranded DNA. In other words, the present inventors have discovered that thioflavin T is a G-quadruplex-specific fluorescence probe. Therefore, situations where a target DNA forms and does not form a G-quadruplex in the presence of potassium ions are each as follows.

(1) Where a Target DNA Forms a G-Quadruplex in the Presence of Potassium Ions

Since the target DNA forms a G-quadruplex after the steps 1 and 2, a strong fluorescence derived from thioflavin T is observed in the step 3. However, a part or all of the target DNA forms a single-stranded DNA or a double-stranded DNA after the step 4, so that in the step 5, a fluorescence derived from thioflavin T is not observed at all, or even if it is observed, its fluorescence intensity value is apparently smaller than the value obtained in the step 3. Therefore, the value obtained in the step 6 is larger than 0.

(2) Where a Target DNA does not Form a G-Quadruplex in the Presence of Potassium Ions Since the target DNA does not form a G-quadruplex either after the steps 1 and 2 or after the step 4, the fluorescence intensities derived from thioflavin T, which are measured in the step 3 and the step 5 are substantially the same. Therefore, the value obtained in the step 6 is substantially 0.

Conditions for destabilizing the structure of a G-quadruplex in the step 4 are, for example, such conditions that lithium ions are present. It is known that the structure of a G-quadruplex is destabilized in the presence of lithium ions. Other conditions for destabilizing the structure of a G-quadruplex are high-temperature conditions. It is known that the structure of a G-quadruplex is destabilized under high-temperature conditions (~100° C.). Conditions for destabilizing the structure of a G-quadruplex in the step 4 are not limited to examples mentioned here. Any conditions that destabilize the structure of a G-quadruplex may be employed.

The wavelength of excitation light used in the step 3 and the step 5 may be any wavelength as long as it is within a range of the absorption band of thioflavin T. However, since the maximum excitation wavelength of thioflavin T is around 450 nm, it is desirable that the wavelength of excitation light used in the step 3 and the step 5 be around 450 nm.

EXAMPLES

DNAs used in Examples and Comparative Examples described below were all purchased from Hokkaido System Science Co., Ltd. Thioflavin T was purchased from Sigma-Aldrich Corporation. Thiazole orange was purchased from Wako Pure Chemical Industries, Ltd. For fluorescence intensity analysis, Varioskan flash manufactured by Thermo Fisher Scientific Inc. was used.

Comparative Example 1

In Comparative Example 1, a G-quadruplex and a double-stranded DNA were detected using thiazole orange as a representative benzothiazole derivative. The G-quadruplex used in this Comparative Example is composed of a DNA of a human telomeric sequence of 5'-GGGTTAGGGTTAGGGT-TAGGG-3' (SEQ ID NO: 3) (hereinafter, a DNA of this sequence is referred to as G-DNA 1). The sequence of the double-stranded DNA used in this Comparative Example was 5'-AGTTCAAGGCGCCTTGAACT-3' (SEQ ID NO: 4) (hereinafter, a DNA of this sequence is referred to as Duplex 1). These two kinds of DNAs were used to conduct experiments as described below. First, a reaction solution shown in Table 1 was prepared.

TABLE 1

| MES-LiOH, pH7 | 50 mM |
| KCl | X mM |
| G-DNA 1 or Duplex 1 | Y µM |
| TO | 1 µM |
| Total volume | 100 µL |

Figure 3:
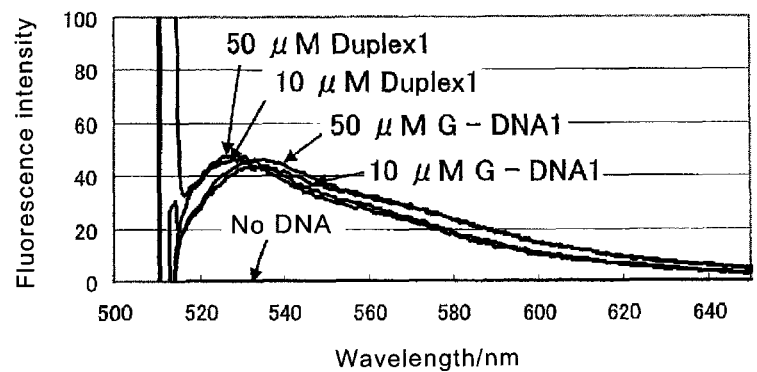
FIGS. 3a and 3b show a graph of fluorescence spectrum results in the presence of 0 mM KCl and a graph of plotting a relationship between each DNA concentration and a fluorescence intensity at 530 nm in the presence of 0 mM KCl in Comparative Example 1.
Figure 3:
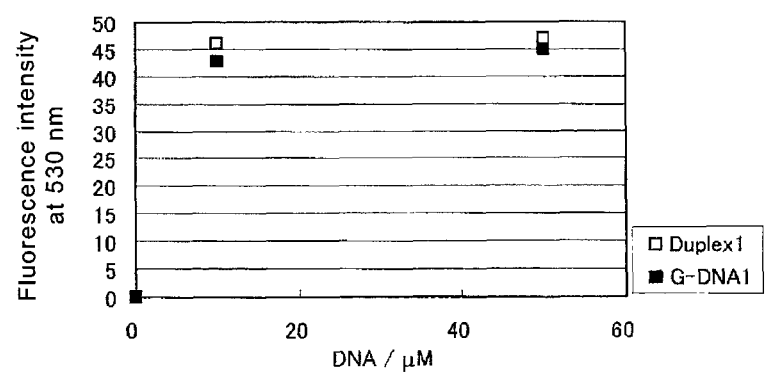
Figure 4:
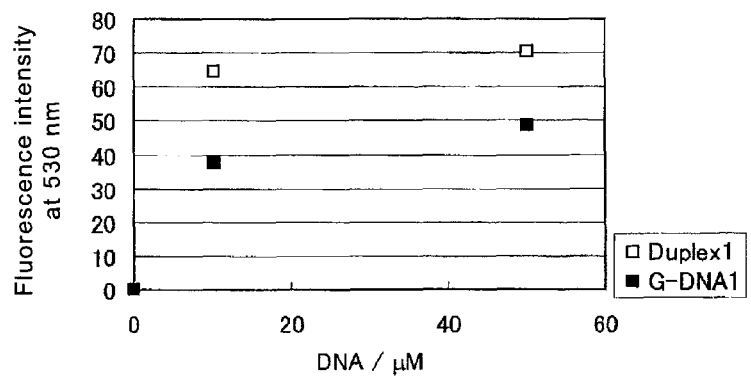
FIG. 4 shows a graph of plotting a relationship between each DNA concentration and a fluorescence intensity at 530 nm in the presence of 50 mM KCl in Comparative Example 1.
Figure 5:
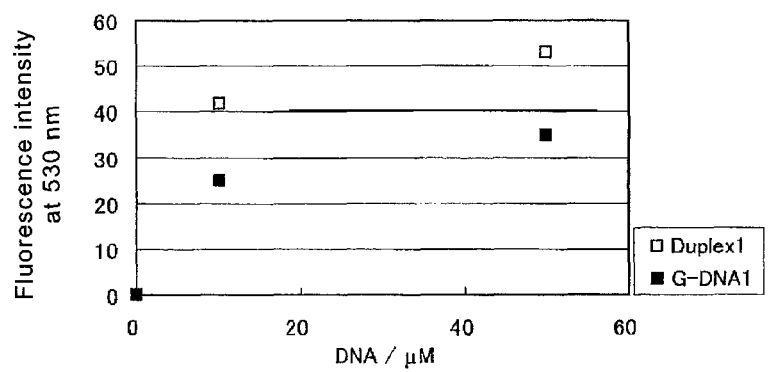
FIG. 5 shows a graph of plotting a relationship between each DNA concentration and a fluorescence intensity at 530 nm in the presence of 100 mM KCl in Comparative Example 1.
Figure 6:
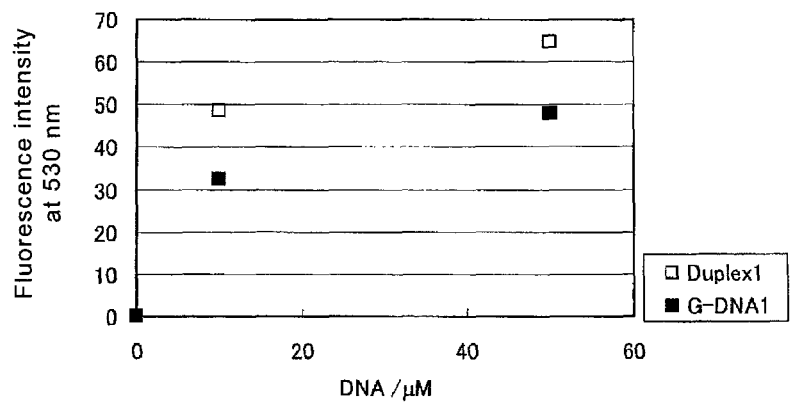
FIG. 6 shows a graph of plotting a relationship between each DNA concentration and a fluorescence intensity at 530 nm in the presence of 150 mM KCl in Comparative Example 1.
Figure 7:
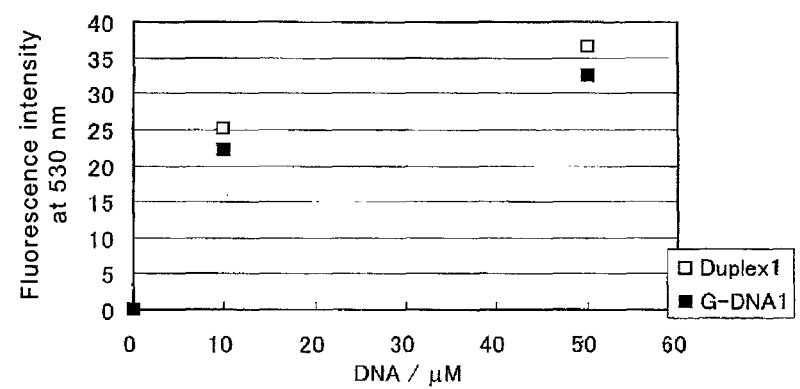
FIG. 7 shows a graph of plotting a relationship between each DNA concentration and a fluorescence intensity at 530 nm in the presence of 500 mM KCl in Comparative Example 1.

X was 0, 50, 100, 150 or 500. Y was 0, 10 or 50. Next, this reaction solution was incubated at 90° C. for 2 minutes, and thereafter cooled to 25° C. at a temperature fall rate of 0.5° C./minute. G-DNA 1 is already known to form a G-quadruplex after the above step. Similarly, Duplex 1 is known to form an intramolecular double-strand structure. Thereafter, a fluorescence intensity analysis was performed for this reaction solution. The excitation light wavelength was 501 nm. The results are shown in FIG. 3. FIG. 3(A) shows fluorescence spectrum results when the KCl concentration is 0 mM. FIG. 3(B) graphically shows a relationship between each DNA concentration and a fluorescence intensity at 530 nm based on the fluorescence spectrum results. Similarly, FIGS. 4 to 7 graphically show a relationship between each DNA concentration and a fluorescence intensity at 530 nm in the presence of 50, 100, 150 and 500 mM KCl, respectively. From the foregoing results, it is revealed that thiazole orange generates a fluorescence when reacted with G-DNA 1, and also generates a comparable or stronger fluorescence when reacted with Duplex 1. That is, these results show that thiazole orange has no specificity to a G-quadruplex. Therefore, thiazole orange cannot be used for analysis on whether or not a target DNA can form a G-quadruplex.

Example 1

In Example 1, G-DNA 1 and Duplex 1 were detected in the same manner as in Comparative Example 1. However, thioflavin T (concentration: 1 μM) was used in place of TO. Only under conditions of 100 mM KCl, 5'-TTTTTTTTTTTTTTTTTTTTT-3' (SEQ ID NO: 5) was used as a DNA to be measured (hereinafter, a DNA composed of this sequence is referred to as T 21). T 21 is known to exist in a solution as a single-stranded DNA. Moreover, the excitation light wavelength was not 501 nm but 450 nm. Otherwise, experiments were conducted in the same manner as in Comparative Example 1.

Figure 8:
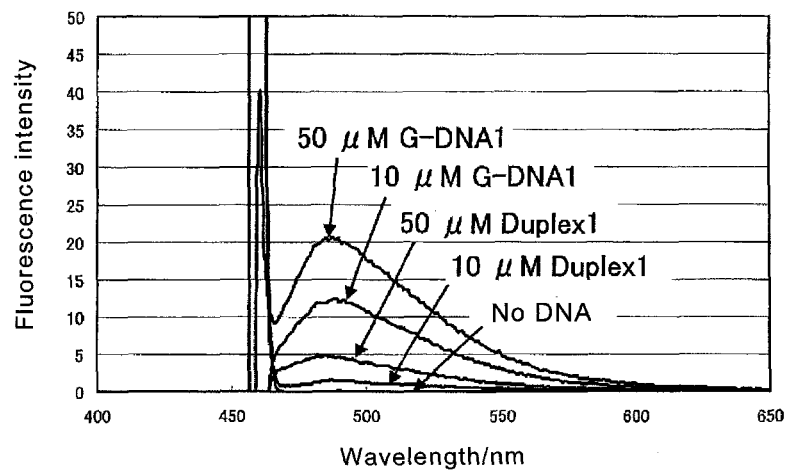
FIGS. 8a and 8b show a graph of fluorescence spectrum results in the presence of 0 mM KCl and a graph of plotting a relationship between each DNA concentration and a fluorescence intensity at 450 nm in the presence of 0 mM KCl in Example 1.
Figure 8:
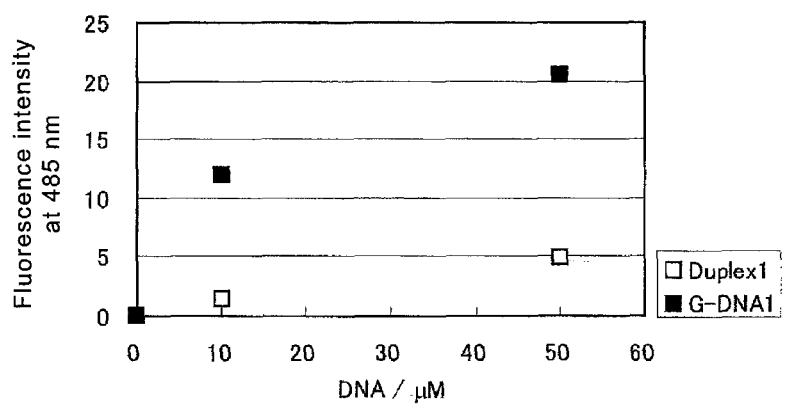
Figure 9:
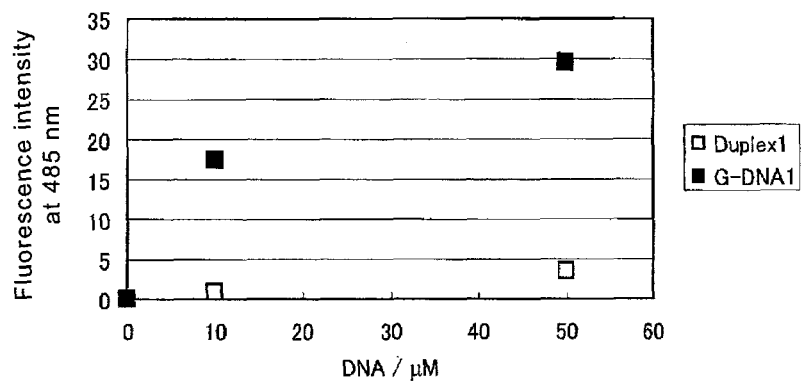
FIG. 9 shows a graph of plotting a relationship between each DNA concentration and a fluorescence intensity at 450 nm in the presence of 50 mM KCl in Example 1.
Figure 10:
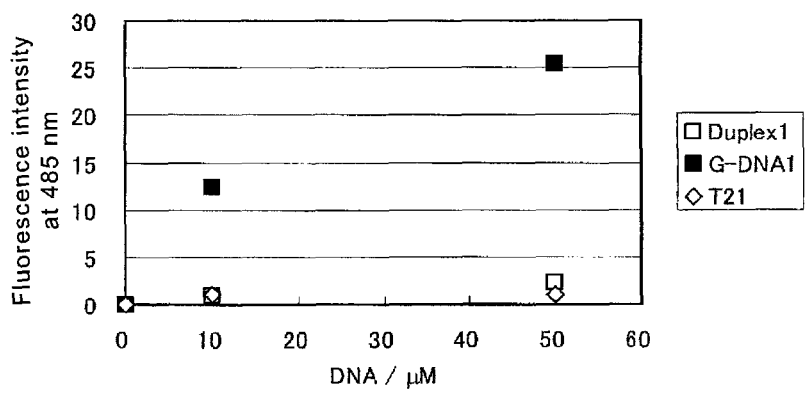
FIG. 10 shows a graph of plotting a relationship between each DNA concentration and a fluorescence intensity at 450 nm in the presence of 100 mM KCl in Example 1.
Figure 11:
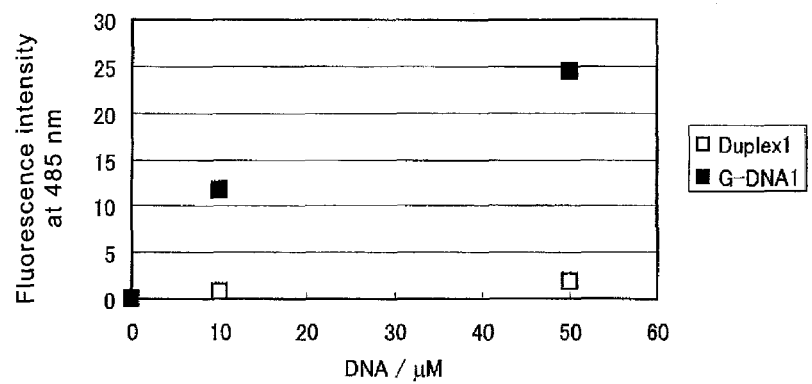
FIG. 11 shows a graph of plotting a relationship between each DNA concentration and a fluorescence intensity at 450 nm in the presence of 150 mM KCl in Example 1.
Figure 12:
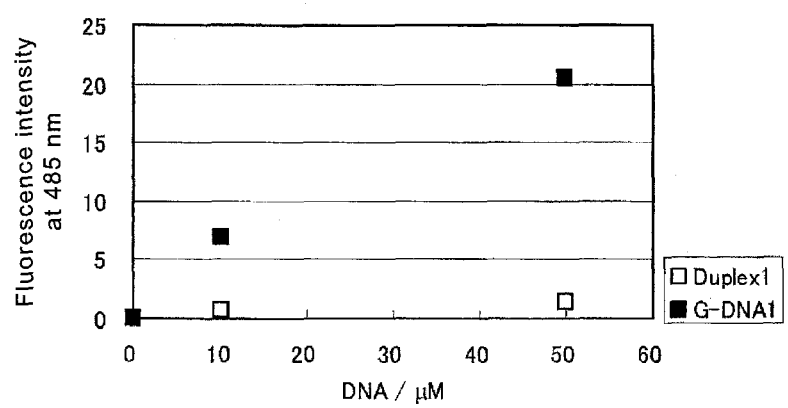
FIG. 12 shows a graph of plotting a relationship between each DNA concentration and a fluorescence intensity at 450 nm in the presence of 500 mM KCl in Example 1.

The results are shown in FIG. 8. FIG. 8(A) shows fluorescence spectrum results when the KCl concentration is 0 mM. FIG. 8(B) shows a graph of plotting a relationship between each DNA concentration and a fluorescence intensity at 485 nm based on the spectrum results. Similarly, FIGS. 9 to 12 show graphs of plotting a relationship between each DNA concentration and a fluorescence intensity at 485 nm in the presence of 50, 100, 150 and 500 mM KCl, respectively. From the foregoing results, it is revealed that thioflavin T generates a fluorescence when reacted with G-DNA 1 in the presence of KCl at any of the concentrations. However, it is revealed that thioflavin T generates little fluorescence when reacted with Duplex 1 or T 21. That is, these results show that the specificity of thioflavin T to a G-quadruplex is extremely high. Therefore, it has been shown that whether or not a target DNA can form a G-quadruplex in the presence of potassium ions can be determined by using thioflavin T.

Example 2

In Example 1, a G-quadruplex composed of G-DNA 1 was detected using thioflavin T. G-DNA 1 is known to form a (3+1)-type G-quadruplex structure (NPLs 3 and 4). In Example 2, a G-quadruplex of different structure was detected using thioflavin T. In Example 2, a G-quadruplex formed by a DNA of a sequence of 5'-GGGGTTTTGGGGTTTTGGGGTTTTGGGG-3' (SEQ ID NO: 6) was a DNA to be measured (hereinafter, a DNA composed of this sequence is referred to as G-DNA 2). The concentration of KCl was 100 mM alone. Otherwise, experiments were conducted in the same manner as in Example 1. G-DNA 2 is known to form an antiparallel-type G-quadruplex under these experimental conditions.

Figure 13:
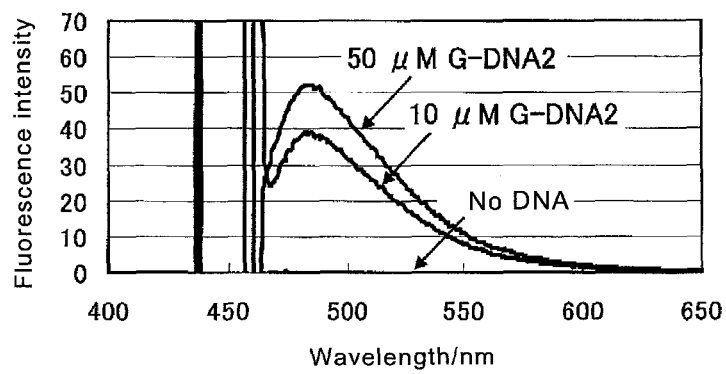
FIGS. 13a and 13b show a graph of fluorescence spectrum results and a graph of plotting a relationship between the concentration of G-DNA 2 and a fluorescence intensity at 450 nm in Example 2.
Figure 13:
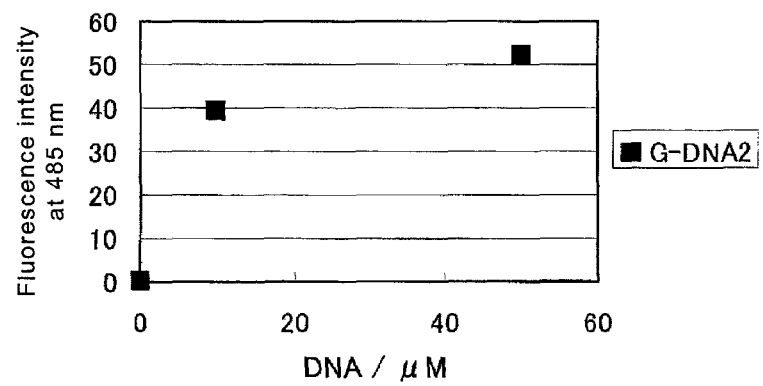

The results are shown in FIG. 13. FIG. 13(A) shows fluorescence spectrum results. FIG. 13(B) shows a graph of plotting a relationship between the concentration of G-DNA 2 and a fluorescence intensity at 485 nm based on the results. From the foregoing results, it is revealed that thioflavin T generates a fluorescence when reacted with G-DNA 2. Therefore, it has been shown that an antiparallel-type G-quadruplex can be detected using thioflavin T.

Example 3

A (3+1)-type G-quadruplex and an antiparallel-type G-quadruplex were detected using thioflavin T in Examples 1 and 2, respectively. Then, in Example 3, a parallel-type G-quadruplex, different from Examples 1 and 2, was detected using thioflavin T. In Example 3, a G-quadruplex formed by a DNA of a sequence of 5'-GGGTGGGTGGGTGGG-3' (SEQ ID NO: 7) was a DNA to be measured (hereinafter, a DNA composed of this sequence is referred to as G-DNA 3). The concentration of KCl was 100 mM alone. Otherwise, experiments were conducted in the same manner as in Example 1. G-DNA 3 is known to form a parallel-type G-quadruplex under these experimental conditions.

Figure 14:
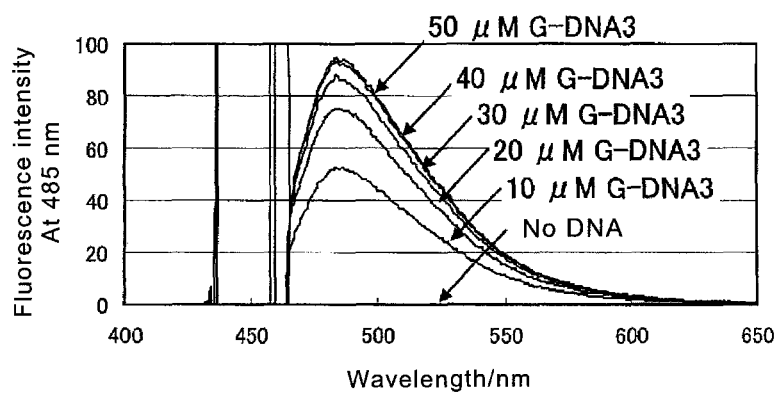
FIGS. 14a and 14b show a graph of fluorescence spectrum results and a graph of plotting a relationship between the concentration of G-DNA 3 and a fluorescence intensity at 450 nm in Example 3.
Figure 14:
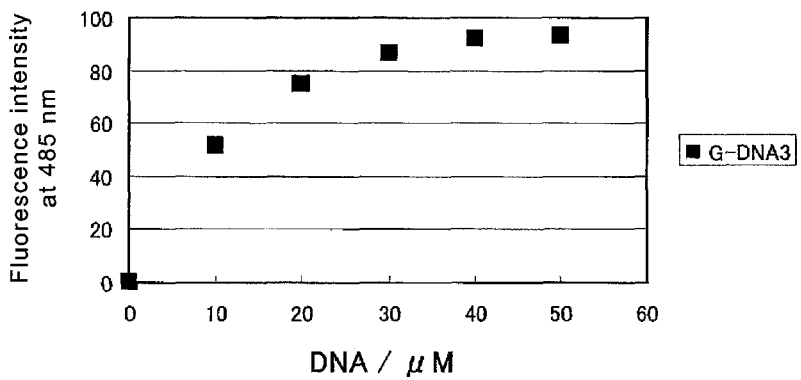

The results are shown in FIG. 14. FIG. 14(A) shows fluorescence spectrum results. FIG. 14(B) shows a graph of plotting a relationship between the concentration of G-DNA 3 and a fluorescence intensity at 485 nm based on the results. From the foregoing results, it is revealed that thioflavin T generates a fluorescence when reacted with G-DNA 3. Therefore, it has been shown that a parallel-type G-quadruplex can be detected using thioflavin T.

Example 4

Figure 15:
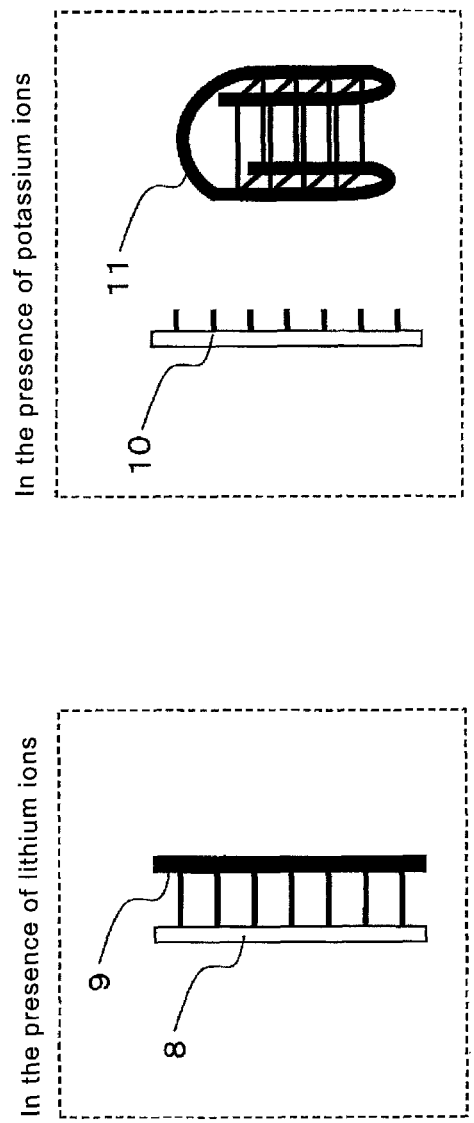
FIG. 15 shows views showing an existential state of G-DNA 2 and Duplex-C in Example 4.

G-DNA 2 and 5'-CCCCAAAACCCCAAAAC-CCCAAAACCCC-3' (SEQ ID NO: 8, complementary strand of G-DNA 2) (hereinafter, this DNA is referred to as Duplex-C) are complementarily bound to each other to form a double-stranded DNA under conditions for destabilizing the structure of a G-quadruplex as in the presence of lithium ions. In the presence of potassium ions, however, G-DNA 2 forms a G-quadruplex structure, and Duplex-C exists in the form of a single-stranded DNA (FIG. 15). In Example 4, whether or not it can be determined that a DNA sample prepared by mixing G-DNA 2 and Duplex-C can form a G-quadruplex in the presence of potassium ions by a difference between a fluorescence intensity derived from thioflavin T in the presence of potassium ions and a fluorescence intensity derived from thioflavin T in the presence of lithium ions was investigated.

The experimental procedure was as follows. First, a reaction solution 1 shown in Table 2 was prepared.

TABLE 2

| | |
|---|---|
| MES-LiOH, pH7 | 50 mM |
| KCl | 100 mM |
| G-DNA 2 | 10 μM |
| Duplex-C | 10 μM |
| Thioflavin T | 1 μM |
| Total volume | 100 μL |

Similarly, a reaction solution 2 was prepared. The composition of the reaction solution 2 was the same as the composition of the reaction solution 1 except that KCl of the reaction solution 1 was changed to LiCl. These reaction solutions were incubated at 90° C. for 2 minutes, and thereafter cooled to 25° C. at a temperature fall rate of 0.5° C./minute. It is already known that after the above step, most of G-DNA 1 in the reaction solution 1 forms a G-quadruplex and Duplex-C exists in the form of a single-stranded DNA. On the other hand, it is known that in the reaction solution 2, lithium ions exist, so that the structure of a G-quadruplex is destabilized, and most of G-DNA 2 and Duplex-C are complementarily bound to each other to form a double-stranded DNA. Thereafter, a fluorescence intensity analysis at 485 nm was performed for these reaction solutions. The excitation light wavelength was 450 nm.

Similarly, as a comparative experiment, the same experiment was conducted except that 5'-AGAAGAGAAAGA-3' (SEQ ID NO: 9) (hereinafter, this DNA is referred to as Duplex-AGA) and 5'-TCTTTCTCTTCT-3' (SEQ ID NO: 10, complementary strand of SEQ ID NO: 9) (hereinafter, this DNA is referred to as Duplex-TCT) were used in place of G-DNA 2 and Duplex-C. Duplex-AGA and Duplex-TCT are complementary to each other. None of them can form a G-quadruplex. Therefore, these DNAs are complementarily bound to each other to form a double-stranded DNA either in the presence of lithium ions or in the presence of potassium ions.

Figure 16:
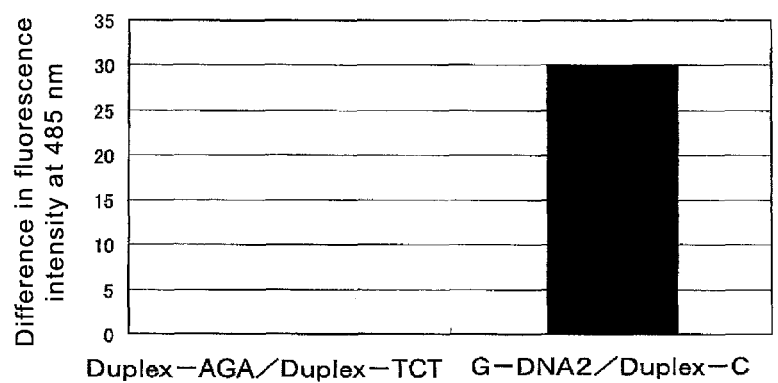
FIG. 16 shows a graph showing a difference in the fluorescence intensity value at 485 nm in Example 4.

The results are shown in FIG. 16. The bar on the right in FIG. 16 shows a value obtained by subtracting a fluorescence intensity value derived from the reaction solution 2 from a fluorescence intensity value derived from the reaction solution 1 when G-DNA 2 and Duplex-C are used. The value was about 30, and larger than 0. On the other hand, the bar on the left shows a value obtained by subtracting a fluorescence intensity value derived from the reaction solution 2 from a fluorescence intensity value derived from the reaction solution 1 when Duplex-AGA and Duplex-TCT are used. The value was about 0. The foregoing results show that whether or not a target DNA can form a G-quadruplex in the presence of potassium ions can be determined using thioflavin T.

Example 5

It is known that most of G-DNA 1 forms a G-quadruplex in the presence of potassium ions. On the other hand, in the presence of lithium ions, the G-quadruplex structure is destabilized, and therefore a part of G-DNA 1 exists in the form of a single-stranded DNA. In Example 1, whether or not a G-quadruplex formed from G-DNA 1 in the presence of potassium ions can be detected using thioflavin T in a sample solution containing G-DNA 1 was investigated. In Example 5, whether or not it can be determined that G-DNA 1 can form a G-quadruplex in the presence of potassium ions by a difference between a fluorescence intensity derived from thioflavin T in the presence of potassium ions and a fluorescence intensity derived from thioflavin T in the presence of lithium ions was investigated.

The experimental procedure was the same as that of Example 4 except that G-DNA 1 was used in place of G-DNA 2 and Duplex-C. As a comparative experiment, an experiment using T 21 in place of G-DNA 2 and Duplex-C was conducted. T 21 exists in the form of a single-stranded DNA either in the presence of lithium ions or in the presence of potassium ions.

Figure 17:
FIG. 17 shows a graph showing a difference in the fluorescence intensity value at 485 nm in Example 5.

The results are shown in FIG. 17. The bar on the right in FIG. 17 shows a value obtained by subtracting a fluorescence intensity value derived from the reaction solution 2 from a fluorescence intensity value derived from the reaction solution 1 when G-DNA 1 is used. The value was about 6, and larger than 0. On the other hand, the bar on the left shows a value obtained by subtracting a fluorescence intensity value derived from the reaction solution 2 from a fluorescence intensity value derived from the reaction solution 1 when T 21 is used. The value was about 0. The foregoing results show that whether or not a target DNA can form a G-quadruplex in the presence of potassium ions can be determined using thioflavin T.

In summary, the present inventor discovered for the first time in the world that specific detection of a G-quadruplex, which could not be achieved by a conventional benzothiazole derivative, can be achieved by using thioflavin T, thus leading to completion of the present invention.

From the description hereinabove, many modifications and other embodiments of the present invention are apparent to persons skilled in the art. Accordingly, the foregoing description should be construed merely as an illustrative example, which was provided for the purpose of teaching best modes for carrying out the present invention to persons skilled in the art. Details of the construction and/or function of the present invention can be substantially altered without departing from the spirit thereof.

INDUSTRIAL APPLICABILITY

The method for specifically detecting a G-quadruplex, according to the present invention, is useful as an analytical method in the field of biotechnology.

REFERENCE SIGNS LIST

1: G-quadruplex
2: G quartet plane
3: Metal ion
4: Chemical structure of G quartet plane
5: Container
6: Sample solution 1 containing potassium ions, target DNA and thioflavin T
7: Sample solution 2 containing target DNA and thioflavin T
8: Duplex-C in double-stranded DNA
9: G-DNA 2 in double-stranded DNA
10: Duplex-C in the form of single-stranded DNA
12: G-quadruplex formed of G-DNA 2

The invention claimed is:

1. A method for determining whether a target DNA forms a G-quadruplex in the presence of potassium ions, wherein the method comprises the following steps of:

retaining a first sample solution containing potassium ions, thioflavin T and the target DNA under G-quadruplex forming reaction conditions; measuring a first fluorescence intensity value A at a wavelength of lambda 1, wherein the first fluorescence intensity value A is derived from thioflavin T contained in the first sample solution, and lambda 1 is 465 nanometers to 505 nanometers; retaining a second sample solution, independent of the first sample solution, containing thioflavin T and the target DNA under conditions for the G-quadruplex to be destabilized; measuring a second fluorescence intensity value B at the wavelength of lambda 1, wherein the second fluorescence intensity value B is derived from thioflavin T contained in the second sample solution; and determining that the target DNA forms the G-quadruplex in the presence of potassium ions if the following inequality is satisfied:

the first fluorescence intensity value $A$–the second fluorescence intensity value $B>0$.

2. The method according to claim 1, wherein it is determined that the target DNA does not form the G-quadruplex in the presence of potassium ions if the inequality of the first fluorescence intensity value A–the second fluorescence intensity value B≤0 is satisfied.

3. The method according to claim 1, wherein the conditions for the structure of the G-quadruplex to be destabilized are such conditions that lithium is present.

4. The method according to claim 1, wherein the lambda 1 is 485 nanometers.

* * * * *